(12) United States Patent
Lindstedt

(10) Patent No.: US 10,357,492 B2
(45) Date of Patent: Jul. 23, 2019

(54) LEVOSIMENDAN FOR USE IN THE TREATMENT OF MOTOR NEURON DISEASES (E.G. ALS)

(71) Applicant: Orion Corporation, Espoo (FI)

(72) Inventor: Ken Lindstedt, Helsinki (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 15/518,949

(22) PCT Filed: Oct. 14, 2015

(86) PCT No.: PCT/FI2015/000039
§ 371 (c)(1),
(2) Date: Apr. 13, 2017

(87) PCT Pub. No.: WO2016/059287
PCT Pub. Date: Apr. 21, 2016

(65) Prior Publication Data
US 2017/0231987 A1     Aug. 17, 2017

(30) Foreign Application Priority Data

Oct. 15, 2014   (FI) ...................................... 20140278

(51) Int. Cl.
*A61K 31/50*   (2006.01)

(52) U.S. Cl.
CPC .................... *A61K 31/50* (2013.01)

(58) Field of Classification Search
CPC ..................................................... A61K 31/50
USPC ...................................................... 514/247
See application file for complete search history.

(56) References Cited

U.S. PATENT DOCUMENTS

2014/0038927 A1 *   2/2014   Cohen .................. A61K 31/137
514/171

FOREIGN PATENT DOCUMENTS

WO   WO 03/004035 A1    1/2003
WO   WO 2012/117073 A2  9/2012

OTHER PUBLICATIONS

Lafci et al., "Protection of the Spinal Cord from Ischemia: Comparative Effects of Levosimendan and Iloprost", 2008, Eur. Surg. Res. , 41(1), pp. 1-7. (Year: 2008).*
Van Hees et al., "Levosimendan Enhances Force Generation of Diaphragm Muscle from Patients with Chronic Obstructive Pulmonary Disease", 2009, Am. J. Respir. Crit. Care Med., 179(1), pp. 41-47. (Year: 2009).*
De Winter et al., "Effect of levosimendan on the contractility of muscle fibers from nemaline myopathy patients with mutations in the nebulin gene", 2015, Skeletal Muscle, 5(DOI: 10.1186/s13395-015-0037-7), pp. 1-10 (Year: 2015).*
International Search Report for International Application No. PCT/FI2015/000039, dated Feb. 15, 2016.
Jonne Doorduin et al., "The Calcium Sensitizer Levosimendan Improves Human Diaphragm Function," *American Journal of Respiratory and Critical Care Medicine*. vol. 185, No. 1, Jan. 1, 2012, pp. 90-95.
Antila, S. et al., Site dependent bioavailability and metabolisms of levosimendan in dogs, 9 European J. Pharmaceutical Sciences 85-91, 90 (1999).

* cited by examiner

*Primary Examiner* — My-Chau T. Tran

(74) *Attorney, Agent, or Firm* — Finnegan, Henderson, Farabow, Garrett & Dunner, L.L.P.

(57) ABSTRACT

The present invention relates to a method of treating motor neuron diseases such as amyotrophic lateral sclerosis (ALS) using levosimendan or its active metabolite (II) as an active ingredient. Levosimendan or its active metabolite (II) are able to relieve the loss of skeletal muscle strength or function associated with motor neuron diseases.

7 Claims, 1 Drawing Sheet

LEVOSIMENDAN FOR USE IN THE TREATMENT OF MOTOR NEURON DISEASES (E.G. ALS)

This is a national stage application under 35 U.S.C. § 371 of International Patent Application No. PCT/FI2015/000039, filed Oct. 14, 2015, which claims the benefit of Finnish Patent Application No. 20140278, filed Oct. 15, 2014, both of which are incorporated herein by reference.

TECHNICAL FIELD

The present invention relates to a method of treating motor neuron diseases and to relieving the loss of skeletal muscle strength or function associated with motor neuron diseases using levosimendan or its active metabolite (II) or any of their pharmaceutically acceptable salts as a medicament.

BACKGROUND OF THE INVENTION

Muscle weakness due to limited neuromuscular input or failure of signal transmission at the neuromuscular junction can result in significant functional disability and increased mortality in several diseases called motor neuron diseases. Such motor neuron diseases include, for example, amyotrophic lateral sclerosis (ALS), spinal muscular atrophy (SMA), Charcot-Marie-Tooth disease (CMT), and myasthenia gravis (MG). Amyotrophic lateral sclerosis (ALS) is a degenerative disease of upper and lower motor neurons that initially leads to progressing muscle dysfunction and ultimately to muscle paralysis. Disease progression is typically fairly linear, and death from respiratory failure occurs 3-5 years from onset. However, there can be variability in the progression rate within individual patients and also in survival between patients (Caroscio J T et al., Neurol Clin 5(1), 1987, 1-8).

Unfortunately, there are few evidence-based options for slowing disease progression or improving quality of life for patients affected by ALS (Miller R G et al., Neurology 73(15), 2009, 1218-1226). Although slowing disease progression is vitally important, a therapy that improves functional performance would benefit patients with ALS even if it does not directly alter the underlying pathophysiologic basis of the disease. Despite significant efforts there are still no therapies on the market that improve neuromuscular function. Thus, if the response of muscle to neural input or the force and endurance of muscle contraction could be enhanced therapeutically, the functional status of ALS patients could be directly maintained or improved, even if their underlying disease process continues.

Levosimendan, which is the (−)-enantiomer of [[4-(1,4,5,6-tetrahydro-4-methyl-6-oxo-3-pyridazinyl)phenyl]hydrazono]propanedinitrile, is currently used for the short term treatment of patients who suffer from acutely decompensated severe heart failure. Levosimendan increases contractility of the heart by enhancing the sensitivity of cardiac myofilaments to calcium. Levosimendan has an active metabolite (R)—N-[4-(1,4,5,6-tetrahydro-4-methyl-6-oxo-3-pyridazinyl)phenyl]-acetamide (II) which is present in man following administration of levosimendan. The sustained hemodynamic effects of levosimendan are due to the active metabolite (II). See Szilagyi S, et al., Eur J Pharmacol. 2004, 486(1):67-74; Kivikko M, et al., Circulation, 2003, 107(1):81-6.

There is an urgent need for medicaments which are able to improve functional status of patients suffering from motor neuron diseases such as ALS.

SUMMARY OF THE INVENTION

It has now been found that oral administration of levosimendan or its active metabolite (II) is able to improve skeletal muscle function in an experimental model of myasthenia gravis. In this model the function of neuromuscular junction is disabled by an antibody which acts against muscular nicotinic acetylcholine receptor and thus produces muscle weakness in animals. The results indicate that levosimendan and its active metabolite (II) are useful in the treatment of diseases with diminished neuromuscular input such as motor neuron diseases.

In one aspect, the present invention a method for the treatment of motor neuron diseases comprising administering to a patient in need thereof levosimendan or its active metabolite (II) or any of their pharmaceutically acceptable salts.

In another aspect, the present invention provides a method for relieving the loss of muscle strength or function in a patient suffering from a motor neuron disease comprising administering to a patient in need thereof levosimendan or its active metabolite (II) or any of their pharmaceutically acceptable salts.

In another aspect, the present invention provides a method for relieving the loss of skeletal muscle strength or function associated with motor neuron diseases in a patient comprising administering to said patient levosimendan or its active metabolite (II) or any of their pharmaceutically acceptable salts.

In another aspect, the present invention provides a compound which is levosimendan or its active metabolite (II) or any of their pharmaceutically acceptable salts for use in the treatment of motor neuron diseases.

In another aspect, the present invention provides a compound which is levosimendan or its active metabolite (II) or any of their pharmaceutically acceptable salts for use in relieving the loss of muscle strength or function associated with motor neuron diseases.

In another aspect, the present invention provides a compound which is levosimendan or its active metabolite (II) or any of their pharmaceutically acceptable for use in relieving the loss of skeletal muscle strength or function associated with motor neuron diseases.

In another aspect, the present invention provides the use of levosimendan or its active metabolite (II) or any of their pharmaceutically acceptable salts in the manufacture of a medicament for use in the treatment of motor neuron diseases.

In another aspect, the present invention provides the use of levosimendan or its active metabolite (II) or any of their pharmaceutically acceptable salts in the manufacture of a medicament for use in relieving the loss of muscle strength or function associated with motor neuron diseases.

In another aspect, the present invention provides the use of levosimendan or its active metabolite (II) or any of their pharmaceutically acceptable salts in the manufacture of a medicament for use in relieving the loss of skeletal muscle strength or function associated with motor neuron diseases.

The motor neuron diseases referred above include, but are not limited to, amyotrophic lateral sclerosis (ALS), myasthenia gravis (MG), spinal muscular atrophy (SMA) or Charcot-Marie-Tooth disease (CMT).

DETAILED DESCRIPTION OF THE INVENTION

Figure 1:
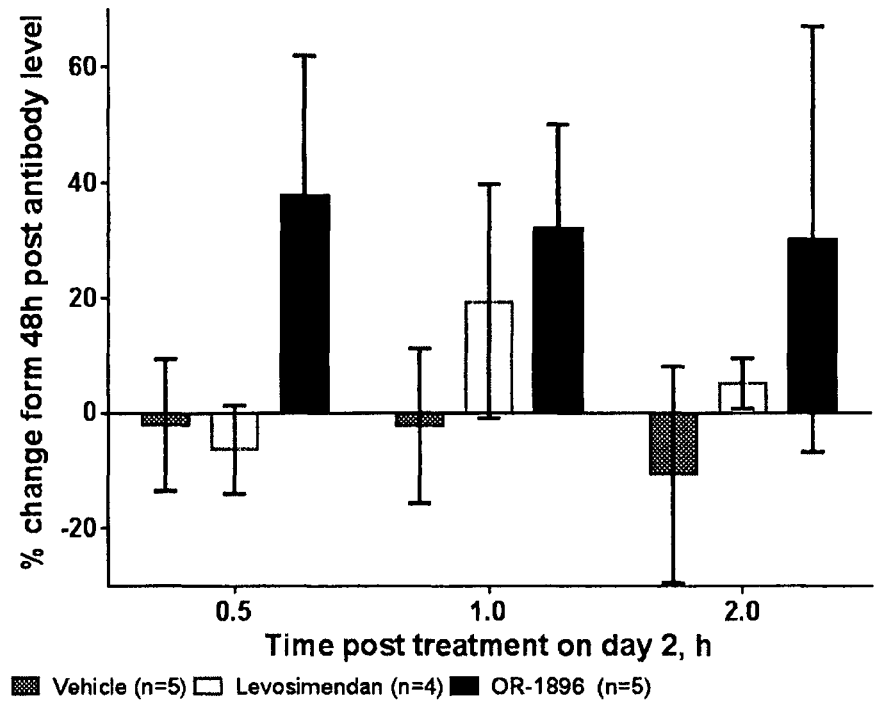
FIG. 1. The effect of drug treatment in myasthenia gravis model. The percent change from the baseline in the length of time the animals were able to stay on the rotating rod (Rotarod) is shown. Measurements were made 0.5 h, 1 h, and 2 h after oral drug treatment on day 2. The treatment groups were vehicle, levosimendan and the active metabolite (II). OR-1896 denotes the active metabolite (II) of levosimendan.

The present invention relates to a method of treating motor neuron diseases and to relieving the loss of strength or function of a muscle, particularly a skeletal muscle, in motor neuron diseases. The term "motor neuron disease" as used herein, refers to diseases that primarily (but not necessarily exclusively) affect motor neurons, neuromuscular input or signal transmission at the neuromuscular junction. The motor neuron diseases referred above include, but are not limited to, amyotrophic lateral sclerosis (ALS), myasthenia gravis (MG), spinal muscular atrophy (SMA) or Charcot-Marie-Tooth disease (CMT). The term "skeletal muscle" as used herein, means a striated muscle that is attached to a bone or other connective tissue, and that typically crosses at least one joint. The term "relieving", as used herein, refers to reducing or inhibiting.

According to one embodiment of the invention, levosimendan or its active metabolite (II) or any of their pharmaceutically acceptable salts is used for relieving the loss of skeletal muscle strength or function associated with motor neuron diseases. According to another embodiment of the invention, said skeletal muscle is a striated muscle that is attached to a bone or other connective tissue and crosses at least one joint. According to still another embodiment of the invention, the joint is a synovial joint.

The administration of levosimendan or its active metabolite (II) or any of their pharmaceutically acceptable salts can be enteral, e.g. oral or rectal; parenteral, e.g. intravenous; or transdermal or transmucosal. Oral administration is a preferred route.

Levosimendan or its active metabolite (II) or any of their pharmaceutically acceptable salts may be administered daily or several times a day or periodically, e.g. weekly or biweekly, depending on the patient's needs.

Levosimendan or its active metabolite (II) may suitably be administered orally to man in a daily dosage ranging from about 0.1 to 10 mg, preferably from about 0.2 to 5 mg, depending on age, weight and the condition of the patient, given once a day or divided into several doses a day. For the long-term treatment of motor neuron diseases in man, relatively low oral doses are generally preferred, e.g. an oral daily dose from about 0.1 to about 5 mg, preferably from about 0.2 to about 4 mg, more preferably from about 0.25 to about 3 mg, for example from about 0.5 mg to 2 mg.

Levosimendan can be administered by intravenous infusion using the infusion rate from about 0.01 to 5 µg/kg/min, typically from about 0.02 to 3 µg/kg/min, for example from about 0.05 to 0.4 µg/kg/min. The active metabolite (II) can be administered intravenously using an infusion rate, which is from about 0.001 to about 1 µg/kg/min, preferably from about 0.005 to about 0.5 µg/kg/min.

According to one embodiment of the invention, the active ingredient of the present invention may be given to a patient suffering from a motor neuron disease together with one or more other active ingredients which are useful in the treatment of motor neuron diseases, for example together with riluzole.

Levosimendan or its active metabolite (II) or any of their pharmaceutically acceptable salts can be formulated into pharmaceutical dosage forms suitable for the treatment according to the present invention using the principles known in the art. The active ingredient of the invention can be given to a patient as such or preferably in combination with suitable pharmaceutical excipients in the form of tablets, granules, capsules, suppositories, emulsions, suspensions or solutions whereby the contents of the active compound in the formulation is from about 0.5 to 100% per weight. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds, release controlling components and other ingredients normally used in this field of technology may be also used.

For oral administration of the active ingredient in tablet or capsule form, suitable carriers and excipients include e.g. microcrystalline cellulose, alginic acid, corn starch, stearic acid, lactose, magnesium stearate, calcium phosphate and talc. For controlled release oral compositions release controlling components can be used. Typical release controlling components include hydrophilic gel forming polymers such as hydroxypropylmethyl cellulose, hydroxypropyl cellulose, carboxymethyl celluloses, or a mixture thereof; vegetable fats and oils including vegetable solid oils such as hydrogenated soybean oil, hardened castor oil or castor seed oil (sold under trade name Cutina HR), cotton seed oil (sold under the trade names Sterotex or Lubritab) or a mixture thereof; fatty acid esters such as triglycerides of saturated fatty acids or their mixtures e.g. glyceryl tristearates, glyceryl tripalmitates, glyceryl trimyristates, glyceryl tribehenates (sold under the trade name Compritol) and glyceryl palmitostearic acid ester.

Tablets can be prepared by mixing the active ingredient or active ingredients with the carriers and excipients and compressing the powdery mixture into tablets. Capsules can be prepared by mixing the active ingredient with the carriers and excipients and placing the powdery mixture in capsules, e.g. hard gelatin or HPMC capsules. Typically a tablet or a capsule comprises from about 0.1 to 5 mg, more typically from about 0.2 to 3 mg, for example from 0.25 to 2 mg, or from 0.25 to 1 mg of levosimendan or its active metabolite (II) or any of their pharmaceutically acceptable salts.

Formulations suitable for intravenous administration such as injection or infusion formulation, comprise sterile isotonic solutions of the active ingredient and vehicle, preferably aqueous solutions. Typically an intravenous infusion solution comprises from about 0.01 to 0.1 mg/ml of levosimendan or its active metabolite (II) or any of their pharmaceutically acceptable salts. The pharmaceutical formulation may be also in the form of an intravenous infusion concentrate to be diluted with an aqueous vehicle before use.

Such concentrate may comprise as a vehicle a pharmaceutically acceptable organic solvent such as dehydrated ethanol.

Salts of levosimendan or its active metabolite (II) may be prepared by known methods. Pharmaceutically acceptable salts are useful as active medicaments, however, preferred salts are the salts with alkali or alkaline earth metals.

EXAMPLES

Pharmaceutical Examples

Example 1. Oral Capsule

| | |
|---|---|
| Levosimendan | 1.0 mg |
| Microcrystalline cellulose | 96.4 mg |
| Alginic acid | 30.0 mg |
| Stearic acid | 5.3 mg |
| Hard gelatin capsule size 3 | |

The pharmaceutical preparation in the form of a capsule was prepared by blending the ingredients and placing the powdery mixture in hard gelatin capsule.

Example 2. Concentrate Solution for Intravenous Infusion

| | |
|---|---|
| (a) levosimendan | 2.5 mg/ml |
| (b) Kollidon PF12 | 10 mg/ml |
| (c) citric acid | 2 mg/ml |
| (d) dehydrated ethanol | ad 1 ml (785 mg) |

The concentrate solution was prepared by dissolving citric acid, Kollidon PF121 and levosimendan to dehydrated ethanol in the sterilized preparation vessel under stirring. The resulting bulk solution was filtered through a sterile filter (0.22 μm). The sterile filtered bulk solution was then aseptically filled into 8 ml and 10 ml injection vials (with 5 ml and 10 ml filling volumes) and closed with rubber closures.

The concentrate solution for intravenous infusion is diluted with an aqueous vehicle before use. Typically the concentrate solution is diluted with aqueous isotonic vehicles, such as 5% glucose solution or 0.9% NaCl solution so as to obtain an aqueous intravenous solution, wherein the amount of levosimendan is generally within the range of about 0.001-1.0 mg/ml, preferably about 0.01-0.1 mg/ml.

Experiment 1.

Effects of Levosimendan and its Active Metabolite (II) in Antibody Induced Myasthenia Gravis Model in Female Lewis Rats.

Methods

The effects of levosimendan and its active metabolite (II) on skeletal muscle weakness were studied in an experimental model of Myasthenia Gravis (Russell A J et al., Nat Med 18 (3), 2012, 452-5). Myasthenia Gravis was induced in female Lewis rats by injecting 500 μg/kg of nAChRα1/3/5 antibody (SC-58604, Santa Cruz Biotechnology) intraperitoneally on day 0. Animals with 40-70% drop in muscle strength from baseline at 48 h after administration of the antibody were randomized into treatment groups: 1) Vehicle control (n=6) (0.5% Methocel 5 ml/kg orally), 2) Levosimendan (n=6) (0.25 mg/kg orally), 3) Active metabolite (II) (n=6) (0.025 mg/kg orally).

Coordination, balance, and motor skill acquisition were tested using an accelerated rotating rod test (Rotarod, Ugo Basile, Comerio, Italy). Rats were placed on a rod that accelerated smoothly from 4 to 40 rpm over a period of 5 min. The length of time that each animal was able to stay on the rod was recorded. Three consecutive measurements were performed. Rats were trained for the test four times one day before and twice on the day of antibody injection. Effects of different drug treatments on Rotarod response were measured 0.5 h, 1 h, and 2 h after oral treatment on day 2, i.e. 48 hours after the induction of Myasthenia Gravis.

Exercise capacity measurements were performed with airtight treadmill (Accupacer treadmill, Accuscan Instruments, USA) connected to a respiratory gas analysing system. Rehearsals and exercise capacity measurements were started with familiarising the rats with the treadmill chambers for 15 minutes (restmill). The exercise program consisted of 15 min running at 10 m/min until the rat was incapable to keep up the speed despite of electric shock motivation. Rats were trained for the test three times one day before and twice on the day of antibody injection. Effects of different drug treatments on treadmill responses were measured 1 h and 2 h after oral treatment on day 3 (72 h after induction of Myasthenia Gravis).

Results

The effects of different drug treatments in Rotarod test are shown in FIG. 1. Levosimendan and its active metabolite (II) produced an acute and transient improvement in muscle function peaking 0.5-1 h after the single oral dosage. Duration of drug responses correlated with the pharmacokinetics of levosimendan (t½ 0.7 h) and active metabolite (II) (in rats t½ 5 h).

Figure 2:
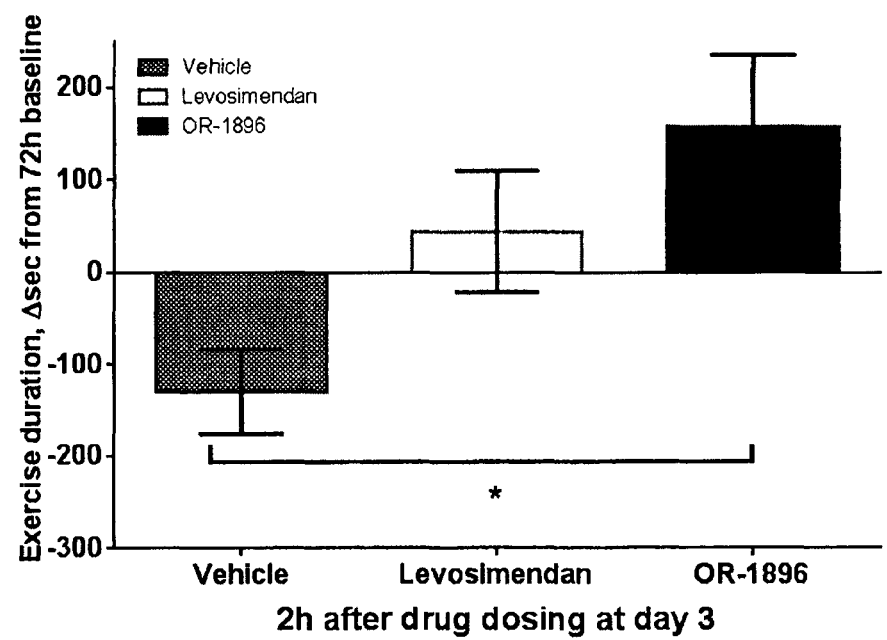
FIG. 2. The effect of drug treatment in myasthenia gravis model. The change in exercise duration of animals running on a treadmill is shown. Measurements were made 2 h after oral drug treatment on day 3. OR-1896 denotes the active metabolite (II) of levosimendan.

The effects of different drug treatments in the treadmill test are shown in FIG. 2. A positive effect of levosimendan and its active metabolite (II) on skeletal muscle function was found at 2 h post-dosing of repeated dosage on day 3.

The invention claimed is:

1. A method for relieving the loss of skeletal muscle strength or function associated with amyotrophic lateral sclerosis (ALS) in a patient in need thereof comprising administering to said patient an effective amount of levosimendan or its active metabolite (II) or any of their pharmaceutically acceptable salts.

2. The method according to claim 1, wherein levosimendan or its active metabolite (II) or any of their pharmaceutically acceptable salts is administered orally.

3. The method according to claim 1, wherein levosimendan or a pharmaceutically acceptable salt thereof is administered.

4. The method according to claim 1, wherein the active metabolite (II) of levosimendan or a pharmaceutically acceptable salt thereof is administered.

5. The method according to claim 1, wherein the skeletal muscle is a striated muscle that is attached to a bone or other connective tissue and that crosses at least one joint.

6. The method according to claim 5, wherein the joint is a synovial joint.

7. A method for relieving the loss of skeletal muscle strength or function associated with amyotrophic lateral sclerosis (ALS) in a patient in need thereof comprising administering to said patient levosimendan or its active metabolite (II) or any of their pharmaceutically acceptable salts in the absence of concurrent administration of other medicament capable of relieving the loss of skeletal muscle strength or function associated with amyotrophic lateral sclerosis (ALS).

\* \* \* \* \*